(12) United States Patent
Krebber

(10) Patent No.: US 6,337,186 B1
(45) Date of Patent: Jan. 8, 2002

(54) METHOD FOR PRODUCING POLYNUCLEOTIDES WITH DESIRED PROPERTIES

(75) Inventor: Claus M. Krebber, Mountain View, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/333,762

(22) Filed: Jun. 15, 1999

Related U.S. Application Data

(60) Provisional application No. 60/089,649, filed on Jun. 17, 1998.

(51) Int. Cl.⁷ .......................... C12Q 1/68; C12P 19/34; C12N 15/00; C12N 9/16; C12N 9/00; C07H 21/02; C07H 21/04

(52) U.S. Cl. ................. 435/6; 435/91.1; 435/91.2; 435/440; 435/196; 435/183; 536/23.1; 536/24.3

(58) Field of Search .................. 435/6, 69.1, 91.1, 435/91.2, 7.6, 440, 196, 183; 530/350; 536/23.1, 23.2, 24.3

(56) References Cited

U.S. PATENT DOCUMENTS

| | | | |
|---|---|---|---|
| 4,959,312 A | 9/1990 | Sirotkin | 435/91 |
| 5,514,568 A | 5/1996 | Stemmer | 435/91.2 |
| 5,605,793 A | 2/1997 | Stemmer | 435/6 |
| 5,811,238 A | * 9/1998 | Stemmer et al. | 435/6 |
| 5,830,721 A | 11/1998 | Stemmer et al. | 435/172.1 |
| 5,834,252 A | 11/1998 | Stemmer et al. | 435/91.1 |
| 5,837,458 A | 11/1998 | Minshull et al. | 435/6 |
| 5,928,905 A | 7/1999 | Stemmer et al. | 435/91.1 |
| 6,096,548 A | 8/2000 | Stemmer | 435/440 |
| 6,117,679 A | 9/2000 | Stemmer | 435/440 |
| 6,132,970 A | 10/2000 | Stemmer | 435/6 |
| 6,165,793 A | 12/2000 | Stemmer | 435/440 |
| 6,180,406 B1 | 1/2001 | Stemmer | 435/440 |

FOREIGN PATENT DOCUMENTS

| | | | |
|---|---|---|---|
| EP | 0285123 A1 | 10/1988 | C12N/15/00 |
| WO | WO 92/18645 | 10/1992 | C12Q/1/68 |
| WO | WO 95/22625 | 8/1995 | C12Q/1/68 |
| WO | WO 96/33207 | 10/1996 | C07H/21/04 |
| WO | WO 97/20078 | 6/1997 | C12Q/1/68 |
| WO | WO 97/35957 | 10/1997 | C12N/1/21 |
| WO | WO 97/35966 | 10/1997 | C12N/15/00 |
| WO | WO 98/13485 | 4/1998 | C12N/15/00 |
| WO | WO 98/13487 | 4/1998 | C12N/15/10 |
| WO | WO 98/27230 | 6/1998 | C12Q/1/68 |
| WO | WO 98/31816 | 7/1998 | C12N/15/55 |
| WO | WO 98/31837 | 7/1998 | C12Q/1/68 |
| WO | WO 99/21979 | 5/1999 | C12N/15/00 |
| WO | WO 99/23107 | 5/1999 | C07H/21/04 |
| WO | WO 99/29902 | 6/1999 | C12Q/1/68 |
| WO | WO 99/41368 | 8/1999 | C12N/15/10 |
| WO | WO 99/41369 | 8/1999 | C12N/15/10 |
| WO | WO 99/41383 | 8/1999 | C12N/15/31 |
| WO | WO 99/41402 | 8/1999 | C12N/15/87 |
| WO | WO 99/51774 | 10/1999 | C12Q/1/68 |
| WO | WO 99/57128 | 11/1999 | C07H/21/04 |
| WO | WO 99/65927 | 12/1999 | C07H/21/00 |
| WO | WO 00/04190 | 1/2000 | C12Q/1/68 |
| WO | WO 00/06718 | 2/2000 | C12N/15/10 |
| WO | WO 00/09682 | 2/2000 | C12N/15/10 |
| WO | WO 00/09727 | 2/2000 | C12N/15/82 |
| WO | WO 00/12680 | 3/2000 | C12N/5/04 |
| WO | WO 00/18906 | 4/2000 | C12N/15/10 |
| WO | WO 00/20573 | 4/2000 | C12N/15/10 |
| WO | WO 00/28008 | 5/2000 | C12N/9/88 |
| WO | WO 00/28017 | 5/2000 | C12N/15/10 |
| WO | WO 00/28018 | 5/2000 | C12N/15/10 |

OTHER PUBLICATIONS

Smith G. the Progeny of sexual PCR. Nature. vol. 370, pp. 325–325, Aug. 1994.*

Prodromou and Pearl. Recursive PCR: a novel technique for total gene synthesis. Protein Engineering vol. 5, No. 8, pp. 827–829, Dec. 1992.*

Sambrook et al. Molecular Cloning: A laboratory manual 2nd Edition. Cold Spring Harbor Laboratory press. Planview, New York. p. 15.14 and p. 15.18, Dec. 1989.*

Ostermeier, M., et al., "A combinatorial approach to hybrid enzymes independent of DNA homologyd" *Nature Biotechnology* vol. 17, Dec. 1999 pp. 1205–1209.

Ostermeier, M., et al., "Combinatorial protein engineered by incremental truncation" *Proc. Natl. Acad. Sci. USA* vol. 96, Mar. 1999 pp. 3562–3567.

Ostermeier, M., et al., "Incremental truncation as a strategy in the engineering of novel biocatalysts" *Bioorganic & Medicinal Chemistry* 7 (1999) pp. 2139–2144.

Michnick, S., et al, "Itching" for new strategies in protein engineering *Nature Biotechnology* vol. 17, Dec. 1999 pp. 1159–1160.

Betton, J–M. et al., "Creating a bifunctional protein by insertion of β–lactamase into the maltodextrin–binding protein," *Nature Biotechnology*, vol. 15, pp. 1276–1279, Nov. 1997.

Bingle, W.H. et al., "A method of tagging specific–purpose linkers with an antibiotic–resistance gene for linker mutagenesis using a selectable marker," *Biotechniques*, 10(2):150–152, Feb. 1991.

Boulain, J.C. et al. "Mutagenesis by random linker insertion in to the lamB gene of *Escherichia coli* K12," *Mol Gen Genet*, 205(2):339–348, Nov. 1996.

(List continued on next page.)

*Primary Examiner*—Stephanie Zitomer
*Assistant Examiner*—Cynthia Wilder
(74) *Attorney, Agent, or Firm*—Norman J. Kruse; Jonathan Alan Quine; Law Offices of Jonathan Alan Quine

(57) ABSTRACT

The invention provides methods for the production of polynucleotides with a desired property (e.g., conferring a desired phenotype and/or encoding polypeptide with a desired property) which is selectable or can be screened for. The method includes making insertions and/or deletions at random sites in DNA segments in a population. In some embodiments the random insertions and deletions are made recursively.

21 Claims, 3 Drawing Sheets

OTHER PUBLICATIONS

Christians, F.C. et al., (1999), Directed evolution of thymidine kinase for AZT phosphorylation using DNA family shuffling, *Nature Biotechnology 17*:259–264.

Crameri, A., et al., (1995), Combinatorial multiple cassette mutagenesis creates all the permutations of mutant and wild-type cassettes, *Biotechniques 18*:194–195.

Crameri, A., et al., (1996), Construction and evolution of antibody–phage libraries by DNA shuffling, *Nature Medicine 2*:100–103.

Crameri, A., et al., (1996), Improved green fluorescent protein by molecular evolution using DNA shuffling, *Nature Biotechnology 14*:315–319.

Crameri, A., et al., (1997), Molecular evolution of an arsenate detoxification pathway by DNA shuffling, *Nature Biotechnology 15*:436–438.

Crameri, A., et al., (1998), "DNA shuffling of a family of genes from diverse species accelerates directed evolution," *Nature, 391*:288–291.

Dassa E., "Sequence–function relationships in Ma1G, an inner membrane protein from the maltose transport system in *Escherichia coli.*," *Mol Microbiol, 7*(1):39–47, Jan. 1993.

Demidov, V. et al., "Sequence selective double strand DNA cleavage by peptide nucleic acid (PNA) targeting using nuclease S1", *Nucleic Acids Res, 21*(9):2103–2107, May 1993.

Dykxhoorn, D.M., et al., "An efficient protocol for linker scanning mutagenesis: analysis of the translational regulation of an *Escherichia coli* RNA polymerase subunit gene," *Nucleic Acids Research, 25*(21):4209–4218 (1997).

Der Vartanian, M., et al., "Permissible peptide insertions surrounding the signal peptide–mature protein junction of the ClpG prepilin: CS31A fimbriae of *Escherichia coli* as carriers of foreign sequences," *Gene, 148*(1):23–32, Oct. 1994.

de Wind, N., et al., "Linker insertion mutagenesis of herpesviruses: inactivation of single genes within the Us region of pseudorabies virus," *J. Virol, 64*(10):4691–4696, Oct. 1990.

Doi, N., et al., "Insertion of foreign random sequences of 120 amino acid residues into an active enzyme," *FEBS Lett, 402*(2–3):177–180, Feb. 1997.

Dube, D.K., et al., "Mutants generated by the insertion of random oligonucleotides into the active site of the beta–lactamase gene," *Biochemistry, 28*(14):5703–5707, Jul. 1989.

Duplay, P., et al., "Linker mutagenesis in the gene encoding the periplasmic maltose–binding protein of *E. coli.,*" *Biochimie, 67*(7–8):849–851, Jul. 1985.

Duplay, P., et al., "Silent and functional changes in the periplasmic maltose–binding protein of *Escherichia coli* K12.I Transport of maltose," *J Mol Biol, 194*(4):663–673, Apr. 1987.

Duplay, P., et al., "Silent and functional changes in the periplasmic maltose–binding protein of *Escherichia coli* K12. Chemotaxis Towards Maltose," *J Mol Biol*, vol. 194, pp. 675–678 (1987).

Encell, L.P., et al., "One small StEP in molecular evolution . . . ," *Nature Biotechnology*, vol. 16, pp. 234–235, Mar. 1998.

Fellay, R., et al., "Interposon mutagenesis of soil and water bacteria: a family of DNA fragments designed for in vitro insertional mutagenesis of gram–negative bacteria," *Gene, 52*(2–3):147–154 (1987).

Gates, C.M., et al., (1996) Affinity selective isolation of ligands from peptide libraries through display on a lac repressor 'headpiece dimer', *Journal of Molecular Biology 255*:373–386.

Hallet, B., et al., "Pentapeptide scanning mutagenesis: random insertion of a variable five amino acid cassette in a target protein," *Nucleic Acids Res, 25*(9):1866–1867, May 1997.

Hanes, J. et al., "In vitro selection and evolution of functional proteins by using ribosome display," *Proc. Natl. Acad. Sci. USA,* 94:4937–4942, May 1997.

Hayes, F., et al., "Insertion Mutagenesis as a Tool in the Modification of Protein Function," *The Journal of Biological Chemistry,* 272(46):28833–28836 (1997).

Heffron, F., et al., "DNA sequence analysis of the transposon Tn3: three genes and three sites involved in transposition of Tn3," *Cell,* 18(4):1153–1163, Dec. 1979.

Heffron, F., et al., In vitro mutagenesis of a circular DNA molecule by using synthetic restriction sites, *Proc. Natl. Acad. Sci. USA,* 75(12):6012–6016, Dec. 1978.

Heinz, D.W., et al., "Accomodation of amino acid insertions in an alpha–helix of T4 lysozyme. Structural and thermodynamic analysis," *J Mol Biol,* 236(3):869–886, Feb. 1994.

Henningfeld, K.A., "A model for topoisomerase I–mediated insertions and deletions with duplex DNA substrates containing branches, nicks, and gaps," *Biochemistry,* 34(18):6120–6129, May 1995.

Ishikawa, F., et al., "Identification by a random linker insertion method of a region which suppresses the transforming activity of the raf oncogene," *Nucleic Acids Symp Ser,* 19:39–42 (1988).

Keefe, L.J., et al., "Accomodation of insertion mutations on the surface and in the interior of staphylococcal nuclease," *Protein Sci,* 3(3):391–401, Mar. 1994.

Luckow, B., et al., "A new method for constructing linker scanning mutants," *Nucleic Acid Res,* 15(2):417–429, Jan. 1987.

Minshull, J., et al., (1999), Protein evolution by molecular breeding, *Current Opinions in Chemical Biology,* 3:284–290.

Newton, S.M., et al., "Topology of the membrane protein LamB by epitope tagging and a comparison with the X–ray model," *J Bacteriol,* 178(12):3447–3456, Jun. 1996.

Patten, P.A., et al., (1997), Applications of DNA Shuffling to Pharmaceuticals and Vaccines, *Current Opinion in Biotechnology* 8:724–733.

Russell, R.B., et al., "Recognition of analogous and homologous protein folds: analysis of sequence and structure conservation," *J Mol Biol,* 269(3):423–439, Jun. 1997.

Schifferli, D.M., et al., "Permissive linker insertion sites in the outer membrane protein of 987P fimbriae of *Escheria coli,*" *J Bacteriol,* 176(4):1099–1110, Feb. 1994.

Sondek, J., et al., "A general strategy for random insertion and substitution mutagenesis: substoichiometric coupling of trinucleotide phosphoramidites," *Proc Natl Acad Sci USA,* 89(8):3581–3585, Apr. 15, 1992.

Spaete, R.R., et al., "Insertion and deletion mutagenesis of the human cytomegalovirus genome," *Proc Natl Acad Sci USA,* 84(20):7213–7217, Oct. 1987.

Stemmer, W.P., "DNA shuffling by random fragmentation and reassembly: in vitro recombination for molecular evolution," Proceedings of the National Academy of Sciences, USA, 91(22):10747–10751, Oct. 1994.

Stemmer, W.P.C., "Rapid evolution of a protein in vitro by DNA shuffling," *Nature,* 370:389–391, Aug. 1994.

Stemmer, W.P.C., "Searching Sequence Space: Using recombination to search more efficiently and thoroughly instead of making bigger combinatorial libraries," *Biotechnology,* 13:549–553, Jun. 1995.

Stemmer, W.P.C., (1995), The evolution of Molecular Computation, *Science 270*:1510.

Stemmer, W.P.C., et al., (1995), Single–step assembly of a gene and entire plasmid from large numbers of oligodeoxyribonucleotides, *Gene,* 164:49–53.

Stemmer, W.P.C., (1996) Sexual PCR and Assembly PCR., *Encyclopedia of Molecular Biology,* VCH Publishers, pp. 447–457.

Stemmer, W.P.C., et al., (1999), Molecular breeding of viruses for targeting and other clinical properties, *Tumor Targeting 4*:1–4.

Sugiyama, J.E., et al., "Membrane topology analysis of *Escherichia coli* mannitol permease by using a nested–deletion method to create mtlA–phoA fusions," *Proc Natl Acad Sci USA,* 88(21):9603–9607, Nov. 1991.

Tatchell, K., et al., "In Vitro Mutation Analysis of the Mating–Type Locus in Yeast," *Cell,* 27:25–35, Nov. 1981.

Vetter, I.R., et al., "Protein structural plasticity exemplified by insertion and deletion mutants in T4 lysozyme," *Protein Sci,* 5(12):2399–2415, Dec. 1996.

Wiegand, R.C., et al., "Specificity of the S1 nuclease from *Aspergillus oryzae,*" *J Biol Chem,* 250(22):8848–8855, Nov. 1975.

Wong, R.S., et al., "Linker–insertion mutagenesis of *Pseudomonas aeruginosa* outer membrane protein OprF," *Mol Microbiol,* 10(2):283–292, Oct. 1993.

Zhang, J., et al., (1997), Directed evolution of a fucosidase from a galactosidase by DNA shuffling and screening, Proceedings of the National Academy of Sciences, U.S.A. 94:4504–4509.

Zhao, H., et al., "Molecular evolution by staggered extension process (StEP) in vitro recombination," *Nature Biotechnology,* 16:258–261, Mar. 1998.#jf139##

SEQUENCE LISTING

```
<160> NUMBER OF SEQ ID NOS: 12

<210> SEQ ID NO 1
<211> LENGTH: 33
<212> TYPE: DNA
<213> ORGANISM: Artificial Sequence
<220> FEATURE:
<221> NAME/KEY:
<222> LOCATION:
<223> OTHER INFORMATION: Cloning vector pBAD-GFPuv

<400> SEQUENCE: 1
aaggagatat acatatggct agcaaaggag aag                          33

<210> SEQ ID NO 2
<211> LENGTH: 36
<212> TYPE: DNA
<213> ORGANISM: Artificial Sequence
<220> FEATURE:
<221> NAME/KEY:
<222> LOCATION:
<223> OTHER INFORMATION: Cloning vector pBAD-GFPuv

<400> SEQUENCE: 2
ttcacaggtc aagcttcatt atttgtagag ctcatc                       36

<210> SEQ ID NO 3
<211> LENGTH: 24
<212> TYPE: DNA
<213> ORGANISM: Escherichia coli
<220> FEATURE:
```

```
<221> NAME/KEY:
<222> LOCATION:
<223> OTHER INFORMATION:

<400> SEQUENCE: 3
ttaagaccca ctttcacatt taag                                   24

<210> SEQ ID NO 4
<211> LENGTH: 23
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 4
ctaagcactt gtctcctgtt tac                                    23

<210> SEQ ID NO 5
<211> LENGTH: 20
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 5
cactctatca ttgatagagt                                        20

<210> SEQ ID NO 6
<211> LENGTH: 20
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 6
actctatcaa tgatagagtg                                        20

<210> SEQ ID NO 7
<211> LENGTH: 20
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 7
tccctatcag tgatagagaa                                        20

<210> SEQ ID NO 8
<211> LENGTH: 20
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 8
ttctctatca ctgataggga                                        20
```

```
<210> SEQ ID NO 9
<211> LENGTH: 40
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 9
tattactcgc ggcccagccg gcctttgctc acccagaaac                    40

<210> SEQ ID NO 10
<211> LENGTH: 37
<212> TYPE: DNA
<213> ORGANISM: Escherichia coli
<220> FEATURE:
<221> NAME/KEY:
<222> LOCATION:
<223> OTHER INFORMATION:

<400> SEQUENCE: 10
tagaattcgg cccccgaggc caatgcttaa tcagtga                       37

<210> SEQ ID NO 11
<211> LENGTH: 90
<212> TYPE: DNA
<213> ORGANISM: Artificial Sequence
<220> FEATURE:
<221> NAME/KEY:
<222> LOCATION:
<223> OTHER INFORMATION: synthetic oligonucleotide encoding a
      polypeptide having an in vivo biotinylation site sequence

<400> SEQUENCE: 11
ggttctgaag gtggtggttc tgctcagcgt ctgttccaca tcctggacgc tcagaaaatc    60
gaatggcacg gtccgaaagg tggttctggt                                    90

<210> SEQ ID NO 12
<211> LENGTH: 90
<212> TYPE: DNA
<213> ORGANISM: Artificial Sequence
<220> FEATURE:
<221> NAME/KEY:
<222> LOCATION:
<223> OTHER INFORMATION: synthetic oligonucleotide encoding a
      polypeptide having an in vivo biotinylation site sequence

<400> SEQUENCE: 12
accagaacca cctttcggac cgtgccattc gattttctga gcgtccagga tgtggaacag    60
acgctgagca gaaccaccac cttcagaacc                                    90
```

METHOD FOR PRODUCING POLYNUCLEOTIDES WITH DESIRED PROPERTIES

This appln claims benefit of Prov. No. 60/089,649 filed Jun. 17, 1998.

FIELD OF THE INVENTION

The present invention relates to methods for the production of polynucleotides conferring a desired phenotype and/ or encoding a polypeptide having an advantageous predetermined property which is selectable or can be screened for.

BACKGROUND OF THE INVENTION

Traditional molecular biological methods for generating novel genes and proteins generally involved rational or directed mutation. An example is the generation of a polynucleotide encoding a fusion or chimeric protein by using known restriction sites to combine functional domains from two characterized proteins. Another example is the introduction of a point mutation at a specific site in a polypeptide. Although useful, the power of these and similar methods is limited by the requirement for sequence or restriction map information to facilitate the mutagenesis, and by the limited number of variants that can be efficiently generated.

An alternative approach to the generation of variants uses random recombination techniques such as "DNA shuffling" (Patten et al., 1997, Curr. Opin. Biotech. 18:724–733). DNA shuffling entails performing iterative cycles of recombination and screening or selection to "evolve" individual genes, whole plasmids or viruses, multigene clusters, or whole genomes. Such techniques do not require the extensive analysis and computation required by conventional methods for engineering of polynucleotides and polypeptides. Moreover, DNA shuffling allows the recombination of large numbers of mutations in a minimum number of selection cycles, in contrast to traditional, pairwise recombination events. Thus, DNA shuffling techniques provide advantages in that they provide recombination between mutations in any or all of these, thereby providing a very fast way of exploring the manner in which different combinations of mutations can affect a desired result.

The present invention provides methods that may be used alone or in combination with random recombination techniques such as DNA shuffling to generate novel polynucleotides having, or encoding a polypeptide having, a desired property or combination of properties.

SUMMARY OF THE INVENTION

In one aspect, the invention provides a method of producing a DNA segment having a desired property or combination of properties by mutating a substrate population. The method involves:
a) mutating a substrate population that includes a plurality of DNA segments by:
  i) making insertions at random sites in the segments (random insertion),
  ii) making deletions at random sites in the segments (random deletion), or both, to produce a mutated population including mutated DNA segments,
b) screening the mutated population to obtain a first selected population that includes at least one DNA segment with a first desired property,
c) mutating the first selected population by making random insertions, random deletions, or both, to produce a recursively mutated population, and,
d) screening the recursively mutated population to obtain a recursively selected population that includes at least one DNA segment with a second desired property.

In some embodiments the method further includes at least one additional cycle of mutation and screening (e.g., mutating the recursively selected population and screening the resulting recursively mutated population to obtain new recursively selected population with a desired property) after step (d). In some embodiments, shuffling of one or a combination of polynucleotides in a recursively selected population is carried out.

In various embodiments, the second desired property may be the same or different from the first desired property, and may be a combination of properties. In some embodiments, the polynucleotides in the recursively selected population have a property that is enhanced when compared to the polynucleotides in the first selected population. In some embodiments the substrate population includes DNA segments encoding a polypeptide, a catalytic RNA, a promoter sequence or a vector. In some embodiments the substrate population is homogeneous. In some embodiments a polynucleotide that encodes a polypeptide is screened for an activity such as an enzymatic activity, a substrate specificity, or a binding activity of a polypeptide.

In another aspect, the invention provides a method of producing a DNA segment having a desired property by:
a) mutating a first substrate population that includes a plurality of DNA segments by:
  i) making insertions at random sites in the segments (random insertion),
  ii) making deletions at random sites in the segments (random deletion), or both, to produce a first mutated population of mutated DNA segments;
b) mutating a second substrate population that includes a plurality of DNA segments by:
  i) making insertions at random sites in the segments,
  ii) making deletions at random sites in the segments, or both to produce a second mutated population of mutated DNA segments;
c) recombining the first substrate population and the second substrate population to produce a recombined population; and,
d) screening the recombined population to identify at least one DNA segment with the desired property.

In one embodiment, the first and second mutated populations are screened to produce a first and second selected population, each having a desired property, and the selected populations are recombined.

In various embodiments, the recombination may be achieved by shuffling or directed recombination. In some embodiments the first desired property and the second desired property are the same. In some embodiments the substrate population includes DNA segments encoding a polypeptide, a catalytic RNA, a promoter sequence or a vector. In some embodiments the substrate population is homogeneous. In some embodiments a polynucleotide that encodes a polypeptide is screened for an activity such as an enzymatic activity, a substrate specificity, or a binding activity of a polypeptide.

In another aspect, the invention provides a method of producing a DNA segment having a desired property by:
a) mutating a substrate population that includes a plurality of DNA segments by:
  i) making insertions at random sites in the segments,
  ii) making deletions at random sites in the segments; or both, to produce a mutated population of mutated DNA segments;

b) screening the mutated population to obtain a selected population that includes at least one DNA segment with the desired property;

c) shuffling at least one DNA segment for the selected population to produce a recombined population;

d) screening the recombined population for a desired property.

In one embodiment, the shuffling involves conducting a polynucleotide amplification process on overlapping segments of at least one polynucleotide from the selected population under conditions under which one segment serves as a template for extension of another segment, to generate a population of recombinant polynucleotides.

In some embodiments the substrate population includes DNA segments encoding a polypeptide, a catalytic RNA, a promoter sequence or a vectors. In some embodiments the substrate population is homogeneous. In some embodiments a polynucleotide that encodes a polypeptide is screened for an activity such as an enzymatic activity, a substrate specificity, or a binding activity of a polypeptide.

DETAILED DESCRIPTION

I. Definitions

Figure 1:
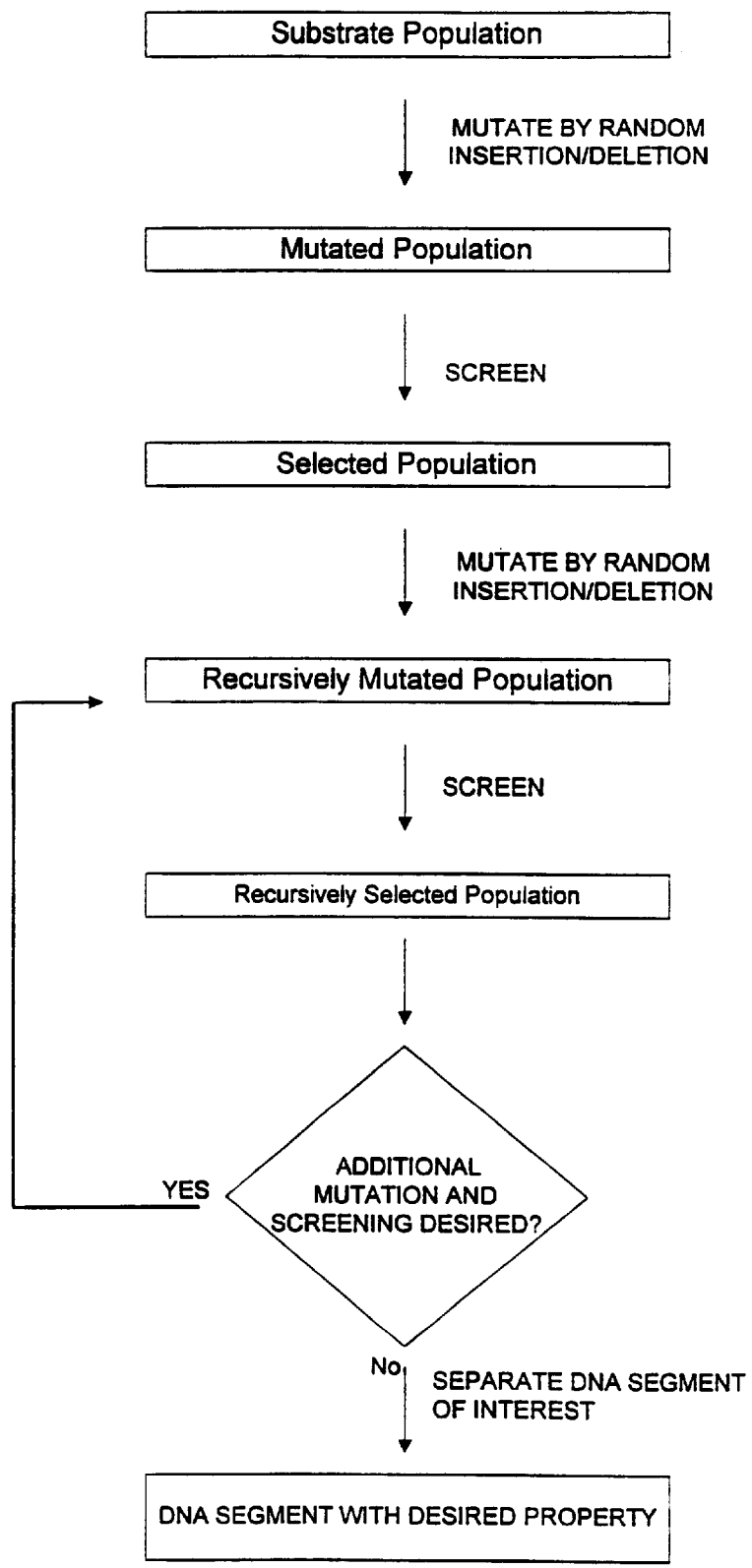
FIG. 1 provides a flow-diagram of an embodiment of the invention in which recursive steps of random insertion or deletion and screening are employed to produce a DNA segment with a desired property.

The following terms are defined to provide additional guidance to one of skill in the practice of the invention:

The term "shuffling," as used herein, refers to techniques for random recombination between substantially homologous but non-identical polynucleotides. Various shuffling methods are described in Patten et al., 1997, *Curr. Opin. Biotech.* 8:724–733; Stemmer, 1994, *Nature* 370:389–391; Stemmer et al., 1994, *Proc. Natl. Acad. Sci. USA* 91:10747–10751; Zhao et al., 1997, *Nucleic Acids Res.* 25:1307–1308; Crameri et al., 1998, *Nature* 391: 288–291; Crameri et al., 1997, *Nat. Biotech.* 15:436–438; Arnold et al., 1997, *Adv. Biochem. Eng. Biotechnol.* 58:2–14; Zhang et al., 1997, *Proc. Nati. Acad. Sci. USA* 94:4504–4509; Crameri et al., 1996, *Nat. Biotechnol.* 14:315–319; Crameri et al., 1996, *Nat. Med.* 2:100–102; PCT publications WO95/22625; WO97/20078; WO97/35957; WO97/35966; WO98/13487; WO98/13485; PCT 98/00852; PCT 97/24239, and references therein. Shuffling techniques are also described in the following U.S. patents and patent applications: U.S. Pat. No. 5,605,793; U.S. patent applications Ser. Nos: 08/537,874; 08/621,859; 08/792,409; 08/769,062; 08/822,589; 09/021,769; 60/074,294; 08/722,660; 08/938,690. Each of the aforementioned patents, applications, and publications is incorporated herein by reference in its entirety and for all purposes. One method of shuffling comprises conducting a polynucleotide amplification process on overlapping segments of a population of variants of apolynucleotide under conditions whereby one segment serves as a template for extension of another segment, to generate a population of recombinant polynucleotides, and screening or selecting a recombinant polynucleotide or an expression product thereof for a desired property. Some methods of shuffling use random point mutations (typically introduced in a PCR amplification step) as a source of diversity.

The term "oligonucleotide," as used herein, generally refers to polynucleotides shorter than about 50 bases (e.g., about 6, 9, 12, 15, 18, 21, 25, 35, or 50 bases in length). The term "polynucleotide," as used herein, refers to both oligo-nucleotides and longer molecules (e.g., at least about 60, 100, 200, 300, 500, 1000, 5000, 10,000 bases or base pairs in length, or even longer. The oligo and polynucleotides used in the present invention are usually DNA molecules, and typically are double stranded.

The term "property," as used herein, refers to any characteristic or attribute of a polynucleotide (or, e.g., an encoded polypeptide or RNA) that can be selected for or detected in a screening system, including, for example, enzymatic or binding activity of a polynucleotide or an encoded polypeptide (e.g., a new activity or enhanced or diminished level of a preexisting activity), fluorescence, properties conferred on a cell comprising a particular polynucleotide, a binding activity (e.g., the property of binding, or being bound by, a specific target molecule, such as receptor, ligand, antibody or antibody fragment, antigen, epitope, or other biological macromolecule). The property may be an attribute of a sequence controlling transcription (e.g., promoter strength, regulation), a sequence affecting RNA processing (e.g., RNA stability or splicing), a sequence affecting translation (e.g., level, regulation, post-transcriptional modification), or a sequence affecting other expression property of a gene or transgene; a replicative element, a protein-binding element; a vector; an encoded protein (e.g., enzymatic activity and specificity, binding activity and specificity, pI, stability to denaturation), an encoded RNA (e.g., mRNA or catalytic RNA), and the like. Additional examples are described herein or in the references incorporated herein, or will be apparent to one of skill upon reading this disclosure.

The term "evolve," as used herein, refers to the process of introducing variation into a population of macromolecules and selecting or screening for acquisition of a desired property or the partial acquisition of a desired property, resulting in the generation of one or more molecules different from the molecules of the starting population.

II. Overview

The present invention provides novel methods for the generation of polynucleotides having a desired property (e.g., an advantageous predetermined property which is selectable or can be screened for). In one aspect, the invention provides methods for generating diversity in a population of polynucleotides by random insertion or deletion of sequences and identification of variants with new or enhanced properties. In some embodiments, multiple cycles of insertion/deletion and screening are carried out. In some embodiments, the properties of the variants are evolved by one or more of a variety of methods.

Typically the mutated polynucleotides are double stranded DNA segments. Examples of suitable DNA segments include DNAs comprising genes, gene fragments, groups of genes, vectors, polypeptide-coding sequences, expression regulatory sequences (e.g., promoters, enhancers), and the like.

In one embodiment of the invention, a population of polynucleotides (i.e., a substrate population) is mutated by random insertion or deletion, and the resulting mutated population is screened to identify a subpopulation of species with a desired property (i.e., a selected population). The selected population is then itself mutated by random insertion or deletion, and the resulting twice mutated population is again subjected to screening to produce a new selected population. The second round of screening can be for the same or a similar property as screened for in the earlier round, or for an entirely different property. For example, when a substrate population of vectors is mutated, the first screen could be for species that have acquired a sequence conferring chloramphenicol resistance not found in the substrate population and the second screen could be for increased chloramphenicol resistance (the same or similar property), or, alternatively, in subsequent rounds of mutation and screening for the acquisition of a sequence conferring tetracycline resistance (a different property). The process of mutation and selection can be carried out for multiple cycles, if desired, to generate one or more novel DNA segments that have a specific desired property or combination of properties. For example, in some embodiments at least 2, 5 or 10 cycles of random insertion/deletion and screening will be carried out. Following two or more cycles of mutation and selection, at least one polynucleotide species having the desired property or properties (e.g., an activity not found in the starting population of polynucleotides) is isolated from the subpopulation. This process is outlined generally in FIG. 1; however, the figure is presented solely to assist the reader and is not intended to limit the invention in any way.

In another embodiment, two or more different substrate populations are mutated by random insertion or deletion, producing corresponding mutated populations. In many embodiments, the two-or-more mutated populations are screened for particular desired properties (e.g., each mutated population is screened for a different property). Following production of the two or more mutated populations (or following screening if it takes place), polynucleotide segments from each of the mutated populations are recombined to produce a single recombined population. The recombination may be carried out by DNA shuffling, or, alternatively, using "classical" molecular cloning techniques in which a selected region in one population of polynucleotides is cloned into a specific site (e.g., a restriction site) in a second population of polynucleotides. "Classical" techniques include (i) restriction of two populations of DNA molecules and ligation of fragments from one of the populations into a restriction site in the DNA of the second population, (ii) amplification of a region of one polynucleotide population (e.g., by PCR or inverse PCR) and ligation into the polynucleotides of the second population, (iii) and other methods known in the art. The recombined population is then screened for the desired property(s). In some embodiments, subsequent cycles of random insertion/deletion or recombination and screening are carried out. This process is outlined in FIG. 2; like FIG. 1, this figure is not intended to limit the invention.

Figure 3:
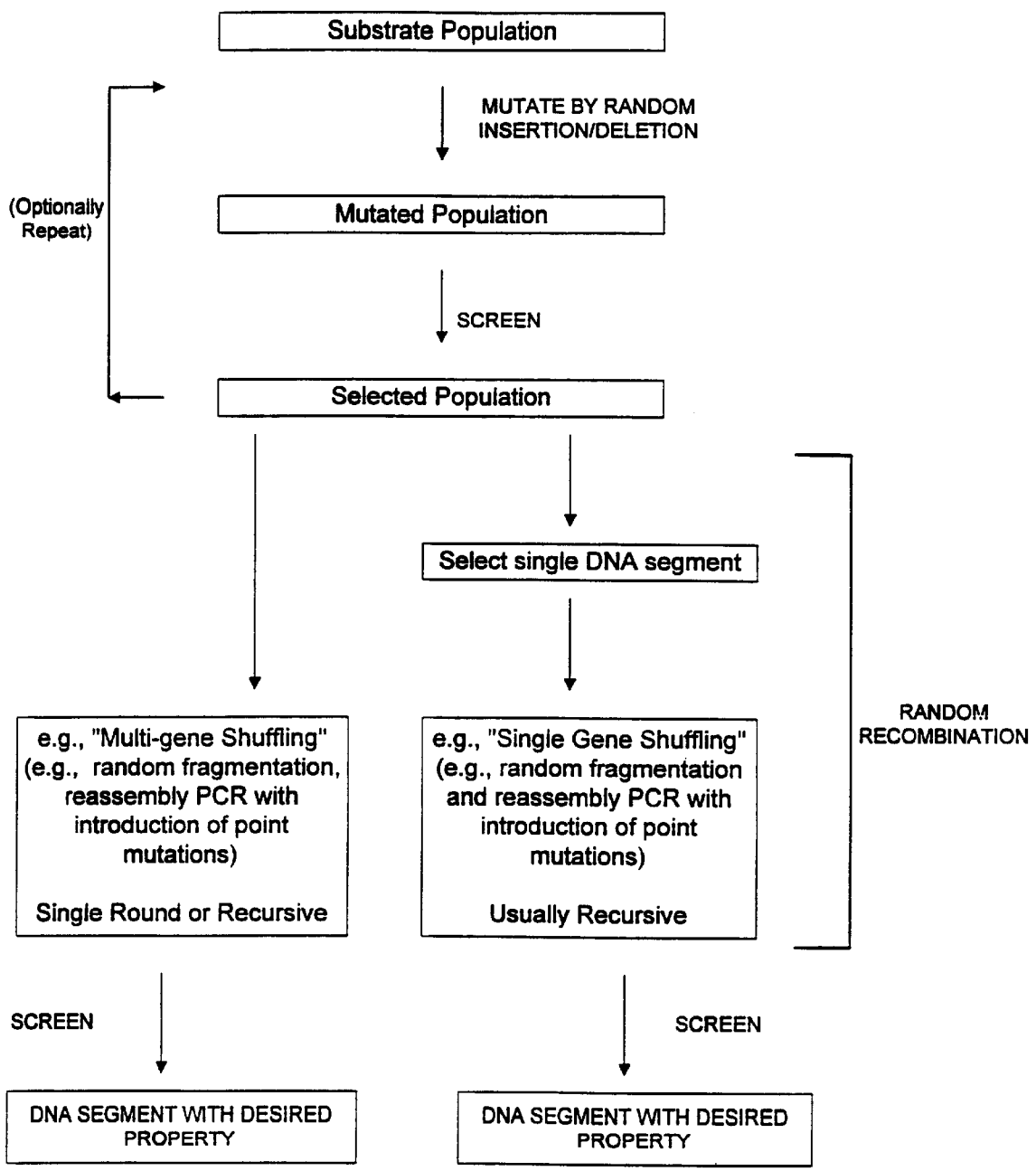
FIG. 3 provides a flow-diagram of an embodiment of the invention in which random insertion or deletion, screening, and random recombination steps are employed to produce a DNA segment with a desired property.

In a third embodiment, a substrate population of polynucleotides is mutated by random insertion or deletion, the resulting mutated population is screened to identify species with a desired property (e.g., a "selected population"). The selected population (or a specie or species isolated from it) is then evolved by random recombination (including random recombination combined with point mutation), which may be recursive or single cycle random recombination. This process is outlined in FIG. 3; this figure also is not intended to limit the invention.

The invention will now be described in greater detail.

III. Mutating the Substrate Population a) Generally

An initial step in the method of the invention is the introduction of insertions or deletions at random sites in a population of polynucleotides. Mutations and deletions are sometimes collectively referred to herein as "mutations." For convenience, a population of polynucleotides into which mutations are to be introduced may be referred to as the "substrate population."

Although the method can be carried out on any polynucleotides that can be mutated in a random fashion by insertion or deletion, as noted supra the polynucleotides will most often be DNA molecules (including cDNA), usually double-stranded DNA molecules. The DNA molecules making up the substrate population may be of any of several types, including DNA molecules comprising polypeptide coding sequences (e.g., encoding a protein, multiple proteins, or portions of a protein), regulatory DNAs (e.g., promoters, enhancers), vectors (e.g., an expression vector), and viruses (e.g., to produce attenuated virions). These DNA molecules are sometimes also referred to as "DNA segments."

The substrate population will comprise a plurality of DNA segments, typically at least $10^2$, more often at least $10^4$, or at least $10^6$ DNA segments. In many embodiments, the DNA segments in any particular substrate population are identical to each other, being derived from a single parental DNA (e.g., plasmid DNAs prepared from the same bacterial culture). Such a population is a "homogeneous" substrate population. In some embodiments, however, the substrate population includes DNA segments that are not identical such as the following: DNA segments that differ from each other by point mutations (e.g., molecules that have been generated from a template using error-prone PCR) or other mutations (e.g., insertions or deletions); DNA segments that are related as homologs from different organisms; and DNA segments that are related to each other because they are products of DNA shuffling reactions (see, e.g., Patten et al., 1997, *Curr. Opin. Biotech.* 8:724). In a related embodiment, the substrate population will comprise DNA segments having unrelated sequences (for example, a substrate population comprising several different plasmid vectors), usually with a plurality (e.g., at least $10^2$ or $10^6$) of each species present.

Mutations (insertions or deletions or both) are introduced into the DNA segments in the substrate population. For convenience, the population of polynucleotides that has been mutated may be referred to as the "mutated population." An important aspect of the present invention is that the mutations are introduced at random sites in the DNA segments. "Random," in this context, has its usual meaning and refers to insertions and deletions that (i) are not made at predetermined sites of a target polynucleotide, and (ii) result in a population of polynucleotides (e.g., a mutated population) in which many different sites of insertion or deletion are represented (i.e., different species in the mutated population comprise insertions or deletions at different sites). In contrast to the random mutations used in the present invention, a mutation is "directed" when it is made at a predetermined site in the polynucleotides in a population, such as the insertion of a cassette into a particular restriction site in the DNA segments of a population, or site-specific mutagenesis.

The art knows a variety of in vitro and in vivo methods for making random insertions and/or deletions in polynucleotides. Although it will be appreciated that the invention is not limited to any specific method for making insertions or deletions, illustrative examples of these methods are provided infra.

Usually the DNA segments to be mutated in vitro are closed circular molecules isolated from cells (e.g., plasmids, circular bacteriophage, and certain vectors) or, alternatively, may be circularized in vitro. Any method of circularization may be used. For example, linear bacteriophage, eukaryotic viruses, PCR products and other linear molecules can be circularized by treatment with DNA ligase or the equivalent. In some embodiments it will be desirable to carry out the ligation reaction at a low concentration of substrate molecules to avoid or reduce concatemerization. In certain embodiments, to limit nuclease activity to single cleavage event per molecule in the subsequent random linearization step (described infra) supercoiled circular DNA is used. Closed circular molecules can be supercoiled by treatment with topoisomerase II (Gellert et al., 1976, *Proc. Nat'l. Acad. Sci.* 73:3872–3876).

In one method of random mutation, the closed circular molecules are randomly cleaved, at a single site. A circular polynucleotide is "linearized" when it is cleaved once (in contrast to a polynucleotide that is "fragmented.") Methods for random linearization are known and include limited hydrolysis of double stranded DNA using double-strand cleaving nucleases (e.g., DNAse I) or using a combination of double-strand DNA nicking enzymes (e.g., DNAse I in the presence of ethidium bromide, topoisomerase mutants) and single-strand specific nucleases (e.g., S1 nuclease, P1 nuclease, Mung Bean nuclease). See, e.g., Yokochi et al., 1996, *Genes Cells* 1:1069–1075; Chaudry et al., 1995, *Nucl. Acids Res.* 23:805–809. Alternatively, "pseudorandom" linearization can be carried out using a relatively non-specific restriction endonuclease (e.g., one that recognizes a common four base sequence) under conditions in which cleavage occurs approximately once per molecule. When necessary, prior to insertion or deletion, protruding ends may be blunted by filling in (e.g., using polymerase and dNTPs) and/or by treatment with exonuclease.

In practice, cleavage of a large population of molecules will usually result in a distribution of polynucleotides in addition to those that are linearized, including some molecules that are uncleaved, and others that are fragmented by cleavage at more than one site. It is known in the art to adjust enzyme and substrate concentrations, digestion times and other conditions to obtain primarily singly-cleaved molecules. If desired, linearized molecules can be isolated from fragments by routine methods (e.g., size selection by gel electrophoresis, chromatography, or centrifugation). However, it is not necessary to separate singly cleaved molecules from those that are uncleaved or multiply cleaved.

b) Random Tnsertions

The polynucleotide or oligonucleotide sequence(s) that are randomly inserted into a population of randomly linearized polynucleotides may be from any of a variety of sources. (The sequence(s) to be inserted can be referred to as the insertion sequence or the "insertion population.") Thus, the oligolpolynucleotides to be inserted may have a defined sequence(s) and/or biological function(s) (e.g., a Drosophila cuticle gene TATA box sequence). Polynucleotides suitable for insertion include defined functional modules or populations of modules (e.g., libraries of promoter, enhancer, or other regulatory elements, sequences encoding T- or B-cell epitopes, biotinylation domains, antibody selectable peptides, protein-binding domains, cellulose binding domains, selectable markers, reporter genes, protein loop sequences, functional domains of a protein, fragments of viral or bacterial genomes, and the like). Polynucleotides suitable for insertion also include defined or undefined fragments of molecules with a known function (e.g., fragments of a known promoter sequence, fragments of polypeptide coding sequences). The oligo/polynucleotides may be of unknown or random sequence and/or biological function, or may have no particular biological function in nature (e.g., a library of random sequence 12 mers).

Suitable insertion polynucleotides may be generated by chemical synthesis, PCR amplification, enzymatic fragmentation, or any other means. The size of the sequence (s) to be inserted may be in a wide range such as at least about 3, 6, 9, 12, 15, 18, 21, 25 or 50 bases in length up to about 0.1, 0.5, 1, or 2 kilobases or even larger. Insertion of the sequence between the termini of a linearized polynucleotide can be carried out by any suitable method. Typically the sequences to be joined are incubated together in the presence of a DNA ligase.

In some embodiments, a single species of polynucleotide (e.g., a 12-mer of a particular sequence) is randomly inserted into a population of polynucleotides. In different embodiments, a plurality (i.e., more than 1) of different species of polynucleotide is introduced in a particular step in the mutation process (e.g., a set of random sequence 12-mers, or a mixture of fragments of a promoter sequence is inserted).

The inserted sequences may modify or supplement the properties of the substrate molecules in any of a variety of ways. They may, as will be apparent from the examples provided infra, be selected to provide a particular sequence, such as a particular epitope coding sequence, protein binding or recognition site, transcription factor binding site, RNA splice site, or the like. Alternatively or in addition, they may act to introduce length variation into a polynucleotide or encoded polypeptide. In an encoded polypeptide, length variations influence the specificity of the molecule (e.g., substrate specificity in an enzyme, antigen specificity in an antibody). In a polynucleotide, length variation will, for example, change the spacing between transcription factor elements in a promoter, profoundly influencing the function of the promoter.

When insertions are made in a protein coding sequence of a polynucleotide, particular techniques can be utilized, if desired, to retain a particular reading frame (e.g., by insuring that the deletions and or insertions will be of a multiple of three nucleotide bases in length). For example, in one embodiment, a single codon (i.e., three nucleotides) is inserted. This can be accomplished by randomly inserting an oligonucleotide having a length that is a multiple of 3 bases (e.g., Boulain et al., 1986, *Mol. Gen. Genet.* 20:339–348). An alternative method involves first randomly inserting a resistance (e.g., drug resistance) cassette which can be cleaved out by restriction endonucleases after selection (e.g., growth on selective media). The insertion cassette can be designed to leave a single or multiple random or non-random codon(s) in the coding sequence (Wong et al., 1993, *Mol. Microbiol.* 10:283–292; Dykxhoorn et al., 1997, *Nuc. Acids Res.* 5:4209–4218; Hallet et al., 1997, *Nuc. Acids Res.* 25:1866–1867). In addition, techniques for co-translational coupling of a reporter gene (e.g., GFP) may be used to identify or eliminate nonproductive (i.e., frame-shifted) products. It will be appreciated that although retaining the original reading frame will reduce the number of "nonproductive" polynucleotides in the mutated population, and thus make screening somewhat more efficient, it is not necessary or always desirable to eliminate frameshift mutations.

c) Random Deletions

In some embodiments of the invention, deletions are introduced at random sites in a substrate population. The introduction of deletions may be used to reduce the size of a polynucleotide sequence (i.e., to increase the insert capacity of a vector), to change a property of a polynucleotide (e.g., by changing the spacing of functional domains in a polypeptide encoded by a DNA segment), and for other purposes.

When a population or polynucleotides is randomly deleted (i.e., deletions are introduced at random locations), there usually will be variation in the extent of deletions in various molecules in the population. The length(s) of deletions introduced in any one step will vary depending in the goals of the investigator, but will typically be less than 100 bases or basepairs (e.g., at least about 3, 6, 9, 12, 15, 18, 21, 25, 35, 50 or 100 bases in length). In some embodiments, however, some or all deletions may be longer, such as at least about 200 or 500 bases.

Deletions may be made by a variety of methods. In one embodiment, a circular or circularized molecule (e.g., a vector) is randomly linearized as described supra. The randomly linearized molecules are then reduced in size (i.e., sequence is deleted) by the use of a processive exonuclease (e.g., Bal31 or exonuclease III). In some embodiments, the resulting linear molecules are blunted by standard methods prior to recircularization by ligation (Sambrook et al., 1989, MOLECULAR CLONING—A LABORATORY MANUAL 2nd ed. Vol. 1–3). In one embodiment, sequences to be inserted (e.g., such as those described supra) can be included in the ligation reaction (resulting in simultaneous insertion and deletion of sequences relative to the substrate population).

In one embodiment of the invention, the polynucleotide is a vector and the introduction of random deletions and selection is used to reduce the size of the vector without eliminating sequences critical for the functioning of the vector (e.g., the replication origin). The reduced size increases the ability to introduce new or larger genes into the vector backbone. When using, for example, a bacteriophage vector with a limited DNA packaging length (due to capsid capacity), the reduction in size of the bacteriophage genome would allow the packaging of new or larger genes without affecting essential phage functions. Notably, the present invention allows reduction in the size of a vector and/or introduction of genes from other sources without a priori knowledge of the function of parts of the parental vector. Thus, it is especially useful when using an uncharacterized bacteriophage as a vector (e.g., for use in Streptomyces bacteriophage ΦC31).

As noted supra, it will sometimes be desirable, when mutating a polynucleotide that encodes a polypeptide, to use techniques to retain a reading frame found in the parental vector. In one embodiment, for example, a single triplet is deleted from (each of) the deleted polynucleotides of a substrate population. This can be carried out by first inserting a resistance cassette which may be excised (e.g., after selection) deleting 3 nucleotides. For example, a cassette or short oligonucleotide containing a Type IIS restriction enzyme recognition site (e.g., EarI, SapI) can be designed which, after random insertion can be cleaved from the circular DNA so that a multiple of 3 nucleotides are removed. Alternatively, mobilization of a transposon (e.g., using cre/lox) may be used to excise the resistance cassette.

d) Additional Methods

In another embodiment of the invention, a mutated population is generated from a substrate population by the introduction of random insertion and/or deletions generated using processive exonuclease digestion of two subpopulations of polynucleotides. The subpopulations are then ligated to produce novel combinations of sequences, as described below.

According to this embodiment, the substrate population may be homogeneous (i.e., a plurality of polynucleotides having the same sequence, e.g., having the sequence of particular gene encoding a protein) or may be non-homogeneous (e.g., containing a mixture of polynucleotides having related sequences, such as a family of related genes [e.g., encoding human actins] or homologs from different species [e.g., encoding human and bovine actin genes], or the product of shuffling reactions, or other non-identical polynucleotides as described supra).

To produce a mutated population having random insertions and/or deletions, the substrate population is divided into at least two subpopulations. A series of nested deletions is produced from each of the, e.g., two subpopulations by incubation with exonuclease using methods well known in the art (see, e.g., Henikoff, 1984, Gene 28:351, see also New England Biolabs Catalog 1998/99 page 129 "Exo-SizeTM Deletion Kit"). Briefly, a nuclease such as exonuclease III is used to create unidirectional deletions in the polynucleotides of each subpopulation. Preferably, restriction endonuclease digestion of the DNA segments in each subpopulation is used to introduce both a nuclease susceptible end (i.e., a 5' overhang or blunt end) and a nuclease nonsusceptible end (i.e., a 3' overhang) such that the nuclease digests in only one direction. The at least two subpopulations differ in that the site of the nuclease susceptible end is different in different subpopulations. After a series of deletions of varying lengths (i.e., nested deletions) is produced in each subpopulation (e.g., by incubating aliquots with exonuclease for differing lengths of time) polynucleotides from each subpopulation are ligated to produce a mixture of mutated polynucleotides having random insertions (e.g., duplications) and/or deletions at the junction site (a mutated population).

An example will help to illustrate this embodiment of the invention. Thus, consider a homogeneous substrate population of DNA segments encoding a polypeptide, which substrate population is divided into two subpopulations. In one embodiment of the method, the nuclease susceptible end in one subpopulation is introduced at the polynucleotide site corresponding to the amino-terminus of the encoded polypeptide with digestion toward the c-terminus, and the nuclease susceptible end in the other subpopulation is introduced at the polynucleotide site corresponding to the carboxy-terminus of the encoded polypeptide, with digestion toward the n-terminus. For purposes of description, the two subpopulations in this illustrative example can be referred to as producing a "amino-terminus deleted" product or a "carboxy-terminus deleted" product.

After a series of nested deletions is produced in each subpopulation, polynucleotides from each subpopulation are ligated to produce a mixture of mutated polynucleotides having random insertions (e.g., duplications) and/or deletions at the junction site. Thus, continuing with the example provided above, and by way of illustration, and not limitation, imagine that in each of the subpopulations deletions range from 1 base to about 99% of the length of the polynucleotide (including, e.g., 5%, 10%, 90% and 95% deletions). It will be appreciated that the ligation of an amino-terminus deleted molecule from which exactly 10% of the length of the molecule is deleted to a carboxy-terminus deleted molecule from which exactly 95% of the length of the molecule is deleted will result in a molecule that has a 5% duplication (at the ligation junction) compared to the substrate polynucleotide sequence. Likewise, the ligation of a amino-terminus deleted molecule from which exactly 5% of the length of the molecule is deleted to a carboxy-terminus deleted molecule from which exactly 90% of the length of the molecule is deleted will result in a molecule that has a 5% deletion (at the ligation junction) compared to the substrate polynucleotide sequence.

It will be apparent that many variations of this basic scheme are available, including, for example, introduction of susceptible ends at sites other than those corresponding to polypeptide termini.

It will be appreciated that the present invention is not limited to any particular method of random insertion or deletion, and that methods other than those specifically described supra may be used. For example, self inserting DNA, i.e., transposons, may be used for in vivo insertion combined with a subsequent in vivo excision by mobilization, or in vitro excision by restriction endonucleases.

It will often be desirable, prior to the screening step (infra), to enrich the mutated population(s) for polynucleotides that have been mutated (i.e., by insertion or deletion). Enrichment is desirable because even efficient methods for insertion and deletion will often result in a mutated population containing some molecules, or even a substantial proportion of molecules, that are wild-type (i.e., do not contain an insertion or deletion). Using an enrichment step will reduce the size of the population that must be subsequently screened. A variety of methods can be used for enrichment. One method, the use of resistance cassettes, is discussed supra. Another suitable method for enrichment of insertion events is carried out by denaturing the DNA of the mutated pool, and subsequently binding it to another aliquot of the inserted DNA which is immobilized on a solid support. Unbound (e.g., wild-type) polynucleotides are removed by washing and the mutated molecules are eluted from the affinity matrix (e.g., using temperature, urea, etc.). Another suitable method for enrichment involves inserting an oligo- or polynucleotide that contains, in addition to the sequence to be inserted, a second sequence, such as a lac operator site, that is bound by an immobilized sequence specific DNA-binding protein (e.g., the LacI repressor). After washing, polynucleotides with the insertion can be eluted (e.g., in the presence of isopropylthiogalactoside). Subsequently the oligo- or polynucleotide sequence responsible for binding can be excised from the polynucleotide, if desired, by a variety of methods, (some of which are discussed supra), leaving behind the sequence to be inserted.

It will be apparent from the description supra that the practice of the invention involves various techniques well known to persons of skill in the art of molecular biology. Instructions sufficient to direct persons of skill through appropriate cloning, sequencing, mutation, random recombination techniques, and other techniques found in, e.g., Berger and Kimmel, Guide to Molecular Cloning Techniques, METHODS IN ENZYMOLOGY volume 152 Academic Press, Inc., San Diego, Calif.; Sambrook et al. (1989) MOLECULAR CLONING—A LABORATORY MANUAL (2nd ed.) Vol. 1–3; and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (1998 Supplement), and other references cited herein and other references known in the art.

IV. Screening a Mutated Population

Another step in the method of the present invention is the screening of a mutated population for a desired property. This results in the identification and isolation of, or enrichment for, DNA segments that acquire the desired property as a result of the mutation (e.g., a new property), or in which an existing property is desirably enhanced. As used herein, the term "screening" has its usual meaning in the art and is, in general, a two-step process. In the first step it is determined whether a DNA segment has a particular property and in the second step the DNA segment(s) with the property are physically separated from those not having the property. For convenience, the population of polynucleotides resulting from the screen may be referred to as the "selected population."

In some forms of screening, identification and physical separation are achieved simultaneously. For example, identification and separation of a polynucleotide conferring drug resistance to a cell can be accomplished by selection of cells resistant to the drug (e.g., culturing under conditions in which non-resistant cells do not survive). It will be clear from this example, that the "separation" step of screening does not imply or require isolation of a biochemically pure polynucleotide with the desired property. Rather, separation means that the DNA segment of interest is separated from other DNA segments (e.g., cells comprising other DNA segments). In some embodiments of the invention, when screening is carried out, the physical separation of DNA segments with the property and those without need not be absolute, and due to methodological limitations often is not. Thus, in some embodiments, the screening of the mutated population results in a selected population that is enriched for the DNA segments with the desired property.

It will be immediately apparent to those of skill that screening requires an assay to identify DNA segments having the desired property. It will also be apparent that the specific assay will depend upon the particular desired property. A variety of examples are provided infra to provide additional guidance to those of skill. Numerous additional screens suitable for use in the present invention are described in publications and disclosures describing "DNA Shuffling" methods. Thus, the reader is referred to the patents, applications, and publications listed in the Section I, supra, in the description of "shuffling," each of which is incorporated herein by reference in their entirety and for all purposes. It will be appreciated, however, the invention is not limited to any particular screening method.

V. Recursive Mutation and Screening

In one embodiment of the invention, the selected population, generated as described supra, is mutated, i.e., insertions, deletions or both are introduced at random sites in the DNA segments in the selected population. The type of mutation may be the same or different from the mutations introduced into the substrate population (i.e., the original or first substrate population). For example, in a case in which random insertions were made in the substrate population, insertions may also be introduced in the selected population or, alternatively, deletions may be introduced. Moreover, when insertions are made, the polynucleotide inserted may be the same or different from the insertion polynucleotide in the previous step. The resulting population of mutated DNA segments may be referred to as a "recursively mutated population" in reference to the fact that the DNA segments have been subjected to more than one cycle of mutation by insertion and/or deletion.

The recursively mutated population is then screened for the desired property. The population of DNA segments resulting from this screen is referred to a "recursively selected population" (i.e., a "first recursively selected population"). The screen used for the "selected population" and the "recursively selected population" may be the same or different. In embodiments in which the same screen is used, the stringency of the screen will be increased to identify DNA segments with increasingly robust properties.

For example, if the desired property is the ability (of a DNA segment) to confer drug resistance to a cell, the second or subsequent screening assay may use a higher concentration of the drug than the initial screen (i.e., the screen of the mutated population). As another example, if the desired property is the ability of a DNA segment to encode a polypeptide that is bound by a particular antibody, increasingly stringent binding conditions may be employed in screens.

Figure 2:
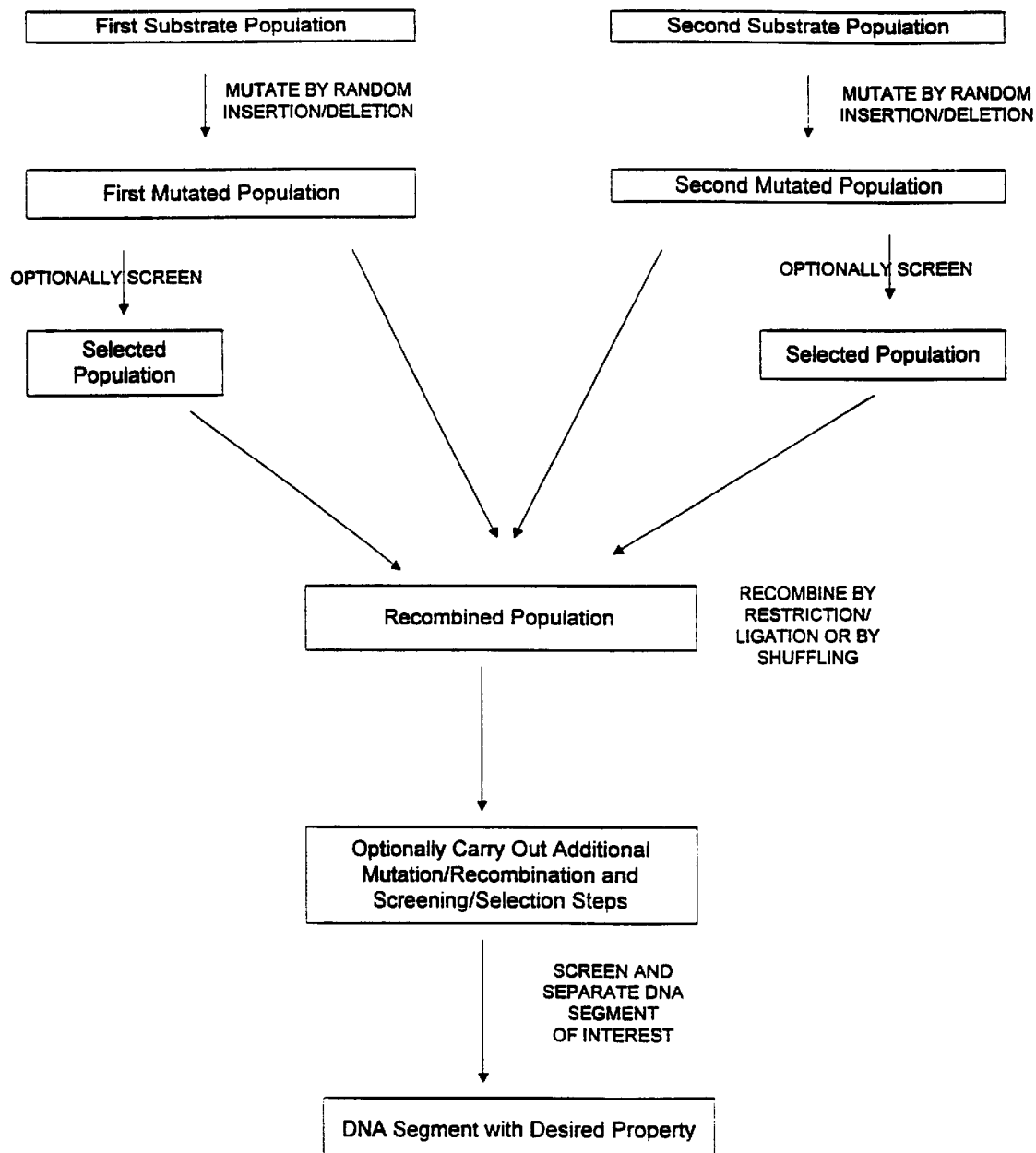
FIG. 2 provides a flow-diagram of an embodiment of the invention in which random insertion or deletion is carried out on two different substrate populations, which are then recombined.

As illustrated in FIG. 1, additional cycles of mutation and screening may be carried out, if desired. Generally, from 1 to 50 additional cycles will be carried out, more often from about 3 to about 10 additional rounds. In cases in which additional cycles of mutation and screening are carried out, it is convenient to refer to the resulting selected populations as the "second recursively selected population," the "third recursively selected population," etc.

As is evident, each of the recursively selected populations contain DNA segments with the desired property. Although in some cases the population as a whole will be useful, more often a particular species of DNA segment will be isolated from the population and used.

VI. Mutation of Multiple Substrate Populations and Screening of Recombinants

In a related embodiment of the invention, random insertions or deletions are introduced into two (or more) different substrate populations and sequence elements from each population are combined by directed recombination or random recombination (e.g., shuffling). Typically, different insertion sequences are introduced into each of the substrate populations. One or each of the mutated substrate populations may be subjected to screening or selection for a particular property conferred by the mutation of that population, prior to the recombination of the substrate populations. Whether or not screening of the mutated substrate populations is undertaken, the recombined population will be subjected to screening/selection for the desired property or combination of properties.

As noted, random recombination methods include DNA shuffling techniques. Shuffling can be carried out in conjunction with the introduction of point mutations (e.g., by error-prone amplification), or without introduction of point mutations (e.g., by the use of proofreading polymerases). In contrast, "directed recombination," or subcloning, refers to methods of recombination that require knowledge of the restriction map of at least part of each substrate population and result in the insertion of a restriction fragment from one population in to a particular restriction site in the second population. Examples include the insertion of particular restriction fragments (by restriction and ligation) or PCR amplicons (usually by ligation or SOE-PCR ["splicing by overlap extension- PCR"]) derived from one substrate population into a specific site or location in the second substrate population, and ligation of two randomly linearized substrate populations.

VII. Random Recombination of the selected Population

In a different embodiment of the invention, the selected population (described in §III, supra), a recursively selected population (described in §V), or a DNA segment species isolated from such a population is used as the starting material for methods which lead to random recombination and point mutation, e.g., DNA shuffling. It will be understood that random recombination refers to recombination methods other than directed exchange of specific defined sequences (e.g., the transfer of a sequence from one population of DNA segments to a second population by restriction and ligation of defined restriction fragments, for example as described in Section VI, supra). Random recombination methods rely instead on the generation of a large pool of DNA fragments by random fragmentation of a single DNA sequence or a family of related DNA sequences, and the reassembly of the fragments in various combinations to produce DNA segments with a new structure (i.e., new combinations of deletions, insertions and/or introduced point mutations) and with the desired property.

Recursive random recombination or non-recursive random recombination methods may be used. The term "recursive" in this context refers to the use of multiple cycles of fragmentation, recombination, and screening (e.g., at least 2, sometimes at least 5 cycles). Typically, when a random recombination method is applied to a single DNA segment from a selected population, a recursive recombination method will be used, e.g., Zhang et al., 1997, *Proc. Natl Acad. Sci.* 94:4504. When a population of different DNA segments are used, both recursive and non-recursive recombination methods (i.e., a single cycle of fragmentation, recombination, and screening) are suitable (see, Crameri et al., 1998, *Nature* 391:288–291).

VIII. Exemplary Applications

This section provides several exemplary examples to illustrate various uses of the invention. Numerous other uses and variations will be apparent to one of skill upon reading the present disclosure.

Exemplary Application 1: Changing Promoter Specificity

In one embodiment, the methods of the invention are used to evolve a transcription regulatory sequence (e.g., a promoter or enhancer sequence) so that the expression characteristics of the regulatory sequence, such as inducibility, tissue specificity, or promoter strength are changed. The use of the methods of the invention is particularly powerful for the evolution of regulatory elements, because such elements are typically modular in structure, with different combinations of modules (or differences in relative orientation) contributing to regulatory activity/function in unpredictable ways.

Typically the mutation and screening of a promoter sequence is carried out using a vector (e.g., an expression vector) in which the target promoter is operably linked to a reporter gene (i.e., a gene encoding a gene product that can be conveniently assayed). Many suitable reporter genes are well known in the art, including the green fluorescent protein (GFP), luciferase, β-glucuronidase, β-galactosidase, and secreted alkaline phosphatase. An advantage of using a promoter-reporter system is that a change in promoter function can be easily detected, facilitating a variety of simple screening methods. Once the promoter sequence is evolved by the present method to have the desired property or combination of properties, the promoter region can be cloned into a different vector (e.g., to drive transcription of a gene of interest other than the reporter gene). Alternatively, the reporter-gene sequence can be removed from the mutated vector and a different gene of interest inserted in its place. Methods for subcloning a promoter or coding sequence in a vector are well known to those of skill in the art (see, e.g., Ausubel et al., supra). For example, the mutated promoter can be amplified by the polymerase chain reaction and the amplified sequence cloned into a region upstream of a selected coding sequence.

Thus, in one exemplary embodiment of the invention, (1) the substrate population is a population of DNA segments having a particular promoter activity (e.g., the ability to direct transcription of a reporter gene in a hepatocyte specific manner) and (2) the desired property is a different promoter activity (e.g., the ability to drive expression in T lymphocytes) or combination of activities (e.g., the ability to drive expression in both T lymphocytes and hepatocytes, but not pancreatic beta-cells). The generation of a lymphocyte-specific promoter, for example, may be carried out by mutating a substrate population comprising a hepatocyte promoter operably linked to a GFP reporter gene, and carrying out a suitable screen of the resulting mutated population.

The promoter sequences are mutated by random insertion and/or random deletion. As described supra, examples of suitable polynucleotides for insertion include random fragments from known promoters (e.g., a T-cell or hepatocyte specific promoter, the metallothionein promoter, the constitutive adenovirus major late promoter, the dexamethasone-inducible MMTV promoter, the SV40 promoter, the MRP polIII promoter, the constitutive MPSV promoter, the constitutive CMV promoter, and promoter-enhancer combinations known in the art), synthetic oligonucleotides constituting modules from known promoters, random sequence polynucleotides, and other sequences. In embodiments in which there is more than one round of mutation, different polynucleotides may be inserted at different steps. For example, the substrate population may be mutated by random insertion of random fragments of a MMTV promoter element and the selected population may be mutated by random insertion of a defined fragment from a metallothionein promoter.

One suitable screen comprises transducing the mutated population of polynucleotides into cultured cells of a particular type (e.g., a Jurkat T lymphocyte cell line), assaying reporter gene expression in the cells (for example by using fluorescence activated cell sorting to detect GFP expression), and selecting cells in which the reporter gene is expressed. Expression in the Jurkat cell type indicates that the mutated hepatocyte promoter segment has acquired the ability to drive transcription in the second cell type. The mutated DNA segments may then be isolated from the population of transduced cells showing the desired property (e.g., new expression specificity), pooled (if not isolated as a pool), and used for additional round(s) of random insertion/deletion mutagenesis or random recombination. Subsequent rounds of mutation and screening may be used to evolve a subpopulation with a higher GFP expression level in Jurkat cells, to add other elements to the promoter (e.g., conferring steroid hormone inducibility). Additional screens may be carried out, if desired, to identify novel promoters with additional desired characteristics. For example, following or concurrently with a screen for the ability of the mutated DNA segments described above to drive expression in T cells, it may be desired to transduce the DNA segment population into hepatocytes and screen for the ability (or lack of ability) to drive transcription in hepatocytes. Using combinations of screens, it is possible to identify novel promoter sequences that, for example, drive expression in T cells and hepatocytes, but not beta-cells. Additional panels of cells types and other variations will be evident to one of skill upon reading this disclosure.

It will be recognized that in the screens described above, control experiments, which will be known to those of skill, will usually also be carried out. If desired, the DNA segment having the new transcription specificity can be isolated from the cell for further manipulation (e.g., it can be operably linked to a variety of coding sequences).

As will be apparent to those of skill, when the mutation step is carried out on a vector comprising the promoter and reporter gene, some of the mutations may disable the reporter gene function (e.g., by introducing a frame shift). In such a case, the "non-productive mutants" in the mutated population will be eliminated in the screening step. Alternatively, the mutation steps may be carried out on a vector containing the promoter only, and following mutation the promoter sequences can be transferred (e.g., by restriction and ligation and/or PCR amplification of the promoter sequence and insertion of the product) as a cassette into a pristine vector comprising a reporter gene. A variety of strategies will be apparent to one of skill following the guidance of this disclosure.

Exemplary Application 2: Changing an Enzymatic Activity

In some embodiments of the invention, the substrate population is a population of DNA segments encoding a polypeptide with an enzymatic activity and the desired property is a new enzymatic activity. In one embodiment, the substrate DNA segments encode a polypeptide with β-galactosidase activity, and the different enzyme specificity desired is fucosidase activity. Recursive rounds of mutation by alternative deletions (of 5–20 basepairs) and insertions (from a library of random hexamers) can be combined with a screen as described in Zhang et al., 1997, *Proc. Natl Acad. Sci.* 94:4504. As noted supra, in cases in which protein coding DNAs are mutated it will often be desirable to use mutation methods that retain the existing reading frame (e.g., deletion and/or insertion of a multiple of 3 nucleotide bases), although, if desired, non-functional frame-shift mutants can be eliminated during the screening step.

Exemplary Application 3: Changing a Property of an Encoded RNA

The methods of the invention may be used to evolve a regulatory element (or other region) of an RNA encoded by the DNA segment. For example, RNA stability elements are known which confer increased stability on mRNAs with which they are physically associated (e.g., encoded downstream of the protein coding sequence). Thus, in one embodiment of the invention, the substrate population is a population of DNA segments that encode mRNA, and the desired property is increased mRNA stability.

The evolution of a mRNA-encoding sequence to encode a more stable RNA is accomplished by randomly inserting DNA sequences into a substrate population encoding an mRNA, and screening or selecting for high levels of expression of the protein (because, generally, expression of the protein product of the gene is proportional to the mRNA stability) or directly assaying the expression level of the mRNA. In one embodiment, the inserted sequences are fragments (e.g., defined or random fragments) of DNA sequences from known stability elements (Chan et al., 1998, *Proc. Nat'l Acad. Sci.* 95:643–6547; Russell et al., 1998, *Mol. Cell. Biol.* 18:2173–2183).

In one embodiment, the increased gene expression in the mutated population is detected and the resulting set of clones (or pools of 2–20 clones having the highest mRNA stability), i.e., the selected population, is used in shuffling or, as a target population for additional mutation. The additional mutation can include insertion of additional downstream mRNA stability conferring fragments (the same as or different from those inserted in earlier steps), deletion and screening for increased mRNA stability, or the insertion of different sequences (e.g., to confer a different selectable property on the RNA-encoding DNA segment).

Exemplary Application 4: Addition of a Functional Domain to a Cloning or Expression Vector In this example, the DNA segments of the substrate population are cloning vectors which may be procaryotic, eukaryotic, or shuttle vectors, and which may be characterized vectors (e.g., pUC18) or uncharacterized vectors. Examples of vectors include artificial chromosomes, plasmids, episomes, viruses, bacteriophages, and mobile elements (e.g. transposons, insertional elements). It is often desirable to add a new functional domain or element to a vector by inserting a cassette encoding a polypeptide (e.g., encoding a resistance marker or novel gene of interest), regulatory element, combinations of genes and regulatory elements, or other functional or structural elements. However, often the optimal location for insertion is not known. It is especially difficult to design vectors with particular or optimal properties when the vectors are complex (e.g., human papilloma virus and other eukaryotic viruses) or intended for use in relatively uncharacterized species of fungi, plants, bacteria (e.g. Streptomycetes), etc. By inserting the function domain, or a fragment thereof, in a random manner, screening the resultant mutant population and optimizing the desired property(s) by recursive insertion/deletion mutation (and, optionally, shuffling), it is possible to efficiently generate vectors with novel and optimized properties.

In one embodiment, an expression cassette (e.g. GFP under control of the *E. coli* lac promoter) is inserted into random positions of the pool of a mixture of randomly linearized vectors (e.g., a pool of pUC19, pET11, pBR322, and pBAD24). Following transformation into host cells (e.g., *E. coli*) the expression of the protein is assayed (e.g., as assessed by its activity, e.g., green fluorescence for GFP), and the clones expressing the highest levels of the reporter gene when induced by IPTG or arabinose are identified and isolated (see, e.g., Crameri et al., 1996, *Nature Biotech.* 14:315–319). DNA shuffling and further screening is carried out. The resulting product is a vector comprising the GFP structural gene positioned in a particular vector backbone at a position that provides the best expression properties of the protein.

Exemplary Application 5: Building an Operon Conferring a Multigenic Phenotype on Cells In another example, the methods of the invention are used to generate a bacterial operon encoding several coding sequences (e.g., genes encoding proteins active in a particular metabolic pathway). Thus, in one embodiment, the coding sequences for each of the polypeptides (e.g., enzymes) to be expressed is inserted in a stepwise fashion (e.g., as outlined in FIG. 1) into a vector comprising one or more promoters able to drive transcription of the polypeptide coding sequences. After each insertion step, a screen is carried out for cells optimally expressing the phenotype conferred by the inserted polypeptide(s). The resulting multigenic operon comprises each of the polypeptide sequences positioned relative to each other, regulatory elements, and other vector elements in positions that result in optimal expression (or other selected-for properties).

Exemplary Application 6: Insertion of an Affinity Selectable Tag into a Polypeptide In another example, a cassette encoding an affinity selectable tag is randomly inserted into a substrate population of DNA segments that comprise a polypeptide coding sequence, resulting in mutant polypeptides that retain biological activity and have acquired the ability to be affinity selected. The addition of an affinity selectable tag to a biologically active protein is useful for, e.g., protein purification.

Examples of sequences that can be randomly inserted into the polypeptide coding sequence of the substrate population include polynucleotides encoding affinity selectable oligo- or polypeptide sequences (e.g., peptide epitopes recognized by an immunoglobulin), anti-antibody fragments (e.g., Vaughan et al., 1996, *Nat. Biotech.* 14:309–314) and others well known in the art. Following insertion, the mutated population is screened and/or selected by a combination assays: typically one assay identifies mutant polypeptides that include the affinity selectable sequence and a second assay identifies polypeptides that have a second biological property (such as the ability to encode a catalytically active enzyme). Screening for affinity (affinity selection) may be carried out by any suitable method, such as affinity chromatography, immunoprecipitation, etc. In some embodiments, a phage display system is used for affinity enrichment. In such systems, the encoded oligo- or polypeptide is presented on the surface of a cell, virus or bacteriophage where it is susceptible to binding by the affinity partner (see e.g., Ernst et al., 1998, *Nucleic Acids Res.* 26:1718–1723; and U.S. Pat. Nos. 5,223,409 and 5,403,484).

Exemplary Application 7: Production of Protein Vaccines

The production of protein vaccines is very often limited by the inefficient expression of the antigenic protein or inefficient processing of the antigen for presentation on MHC complexes. This can be overcome by insertion of one or several epitope sequences from the antigen into a well expressed or efficiently processed protein. Thus, in one approach, multiple T-cell and/or B-cell epitopes are inserted into a known protein "scaffold." In one embodiment, the present invention is used to produce effective vaccines by the insertion of immunodominant T-cell and B-cell epitopes of an immunogenic protein in the scaffold of a highly expressible protein.

In an exemplary embodiment, a known B-cell epitope from HIV gp 120 is inserted into a human scFv protein (Vaughan et al., 1996 *Nature Biotechnology* 14:309–314) and expressed in *E. coli*. The presence of the B-cell epitope in the chimeric protein is screened for as described in copending U.S. Ser. Nos. 09/021769 and 60/074,294. Positive clones (i.e., from the selected population) are pooled and all positive clones are used for the next round of insertion of additional B-cell epitopes and/or T-cell epitopes. DNA shuffling is carried out using DNA from individual clones. The resulting polypeptide comprises multiple well-expressed and well-processed immunogenic peptides and is useful as a vaccine.

IX. EXAMPLES

The following examples are provided to illustrate the practice of the invention.

EXAMPLE I

Synthesis of a Bacterial Vector Containing a New Regulatable Promoter

This example demonstrates the use of the invention to produce a vector with novel properties. Beginning with a known vector (pAK400-GFP) capable of expressing green fluorescent protein (GFP), a process including two cycles of random insertion/deletion mutation and selection or screening are used to produce a panel of novel vectors. The new vectors have new (compared to the parental vector) desired properties with respect to tetracycline resistance, inducibility, and GFP expression levels.

A) Synthesis of Randomly Linearized pAK400-GFP

The parental vector pAK400-GFP is based on the pAK400 vector (Krebber et al., 1997, *J. Immunol. Meth.* 201:35–55), but is modified by replacement of sequences encoding the $tet^R$ (tetracycline resistance) gene with the coding sequence for green fluorescent protein (GFP). To construct pAK400-GFP, GFP is PCR amplified by primers "GFP.For" and GFP.Rev" from pBADGFP cycle 3 (Crameri et al., 1996, *Nature Biotech.* 14:315–319) and cloned by NdeI and HindIII in a three fragment ligation into a NdeI and HindIII vector fragment of pAK400, resulting in "pAK400-GFP." In pAK400-GFP, expression of GFP is under the control of the lac promoter and is inducible by isopropylthiogalactoside (IPTG). The vector also contains an *E. coli* pUC derived ColE1 origin of replication, a lacI gene for the expression of the lac repressor in order to repress the lac promoter efficiently, an f1 origin for packaging of single stranded DNA in phagemids, and the gene for chloramphenicol acetyl transferase which confers resistance to chloramphenicol ($Cam^R$).

Supercoiled pAK400-GFP is prepared in *E. coli* by CsCl/ethidium bromide equilibrium centrifugation according to standard procedures (e.g., Sambrook et al., supra). The vector is linearized by random cleavage by treatment with DNAse I in the presence of ethidium bromide, as described in Chaudry et al., 1995, *Nucleic Acids. Res.* 23:3805–3809. Following phenol/chloroform extraction, the once randomly nicked vector is treated with S1 nuclease at low pH to cleave opposite the single stranded nick (Chaudry et al., supra). The randomly linearized vector is extracted using phenol/chloroform, precipitated and treated with a polymerase (to ensure the DNA is blunt ended) and with alkaline phosphatase (to dephosphorylate the linearized molecules to prevent self-ligation). Finally the linearized (i.e., once cleaved) molecule is purified on a 5% polyacrylamide gel or by CsCl/ethidium bromide equilibrium centrifugation (Sambrook et al., supra).

B) Synthesis of $tet^R$ polynucleotides for random insertion

The tetRA operon containing the $tet^R$ (tetracycline resistance) gene of Tn10 (Schollmeier et al., 1984, *J. Bacteriol.* 160:499–503) is PCR amplified from pAK400 (Krebber et al, 1997, *J Immunol. Meth.* 201:35–55) using the phosphorylated primers Tet.For and Tet.Rev and a proofreading polymerase (Pfu; Stratagene).

C) Tnserting randomly the tet operon into pAK400-GFP

The blunt ended products of (A) and (B), supra, are ligated to each other according to standard procedures (Sambrook et al., supra).

D) Selecting for tetracycline and chloramphenicol resistance and screening for inducihility of GFP by IPTG The ligation reaction of step (C) is transformed into an *E. coli* K12 strain. The transformed cells are plated and selected on LB agar containing chloramphenicol, tetracycline and IPTG ("IPTG plates"). After growth overnight at 37° C., colonies are selected on the basis of green fluorescence upon exposure to UV light (Crameri et al., 1996, *Nature Biotech.* 14:315–319), indicating expression of GFP. The GFP-expressing colonies are replica plated onto agar plates containing chloramphenicol, tetracycline, and 2% glucose ("glucose plates") and assayed for GFP expression (by inspection under V irradiation). DNA is prepared from 100 colonies that express GFP on IPTG plates (initial plating) but not on glucose plates (replica plating). These DNA segments compromise a population of different (in respect to the position of the tetRA-operon) vectors with the phenotype: CamR, $Tet^R$, IPTG-inducible expression of GFP (i.e., IPTG inducible promoter). The vectors in this population may be referred to as pAK400-GFP-Tet. As noted supra, the tetR gene is inserted in different positions in different species in the population.

E) Synthesis of double stranded oligonucleotides from the tet regulatory unit of Tn10

Non-phosphorylated double-stranded oligonucleotides (the pairs of Op1.For/Op1.Rev and Op2.For/Op2.Rev) which encode the two operators of the tn10 promoter (Bertrand et al, 1983, *Gene* 23:149–156) are synthesized chemically. Together the two oligonucleotides are referred to as the "tet oligonucleotides."

F) Ligation of the tet oligonucleotides into the linearized vector pAK400-GFP and swapping of the promoter region into pAK400-GFP-Tet In this and the following steps, the tet oligonucleotides are randomly inserted into linearized pAK400 vector (linearized as described for the pAK400-GFP vector in step A, supra, but not dephosphorylated) to produce a population of pAK400 vectors containing random insertions of the oligonucleotides. Subsequently the (mutated) lac promoter regions from the population (containing insertions) are transferred to the population of pAK400-GFP-Tet vectors made in step D, supra.

(An alternative strategy would be to randomly insert into the pAK400-GFP-Tet vector population. The strategy used is preferred because it requires screening fewer clones, i.e., only clones in which the tet oligonucleotides have inserted at random sites within the lac promoter region rather than in other sites in the vector.)

As a first step, the concentration of double stranded tet oligonucleotides is optimized by ligating different amounts of oligonucleotide into the randomly linearized vector, followed by transformation into an appropriate *E. coli* K12 strain. After growth overnight at 37° C., the colonies are counted. The optimal concentration of oligonucleotide is that concentration that just decreases the number of colonies. Although optimizing the oligonucleotide concentration will increase efficiency, this step is not critical.

Having determined the optimal oligonucleotide concentrations for insertion into the randomly linearized pAK400 (from above), the double-stranded tet oligonucleotides encoding parts of the tet promoter region are inserted into the randomly linearized pAK400 vector by blunt end ligation. After phenol/chloroform extraction, the resulting ligation is cut with KpnI and NdeI at unique sites flanking the lac promoter of pAK400. The resulting fragments containing the lac promoter and a tet promoter oligonucleotide are isolated using electrophoresis in a non-denaturing 8% polyacrylamide gel (Sambrook et al., supra). The KpnI-NdeI fragment from pAK400 is 209 bp. When a 20 basepair oligonucleotide is inserted, the lac promoter fragment will increase in size to 229 bp. Accordingly, a 229 bp band is isolated from the non-denaturing gel. The isolated fragment is cloned (ligated) into the pAK400-GFP-TET vector pool, which has been KpnI and NdeI digested. The result is that some (though usually not all) of the resulting ligation products will comprise a randomly mutated lac promoter (i.e., containing random insertions of the tet promoter oligonucleotide) in a pAK400-GFP vector that is also randomly mutated (i.e., by random insertion of tetRA operon).

G) Selecting for tet and cam resistance and screening for inducibility of GFP by IPTG and/or tetracycline The ligation of step (F) is transformed into an appropriate *E. coli* K12 strain. The transformation is plated and selected on agar plates containing 30 µg/ml chloramphenicol, 5 µg/ml tetracycline, and 2% glucose. The colonies are grown overnight at 37° C.

The recombinants are screened to identify vectors which have different promoters. The expression of GFP in the presence and absence of IPTG and/or tetracycline is determined as described infra. Tetracycline and chloramphenicol resistant colonies are selected by growth in the presence of these two antibiotics. The resistant colonies are replica plated on to four different plates. All plates contain chloramphenicol (to select for the Cam$^R$ of the pAK400 vector backbone). Plate 2 additionally contains IPTG, Plate 3 additionally contains tetracycline, and Plate 4 additionally contains tetracycline and IPTG.

Expression of the GFP reporter gene by colonies is detected by visual or electronic observation of green fluorescence of colonies exposed to UV light (Crameri et al., 1996, *Nature Biotech.* 14:315–319). Colonies that express GFP on one plate and not on one of the others are regulated by either IPTG and/or tetracycline. Compared to the parental vector (which is exclusively regulated by the presence or absence of IPTG) colonies in which GFP expression is either increased or decreased by the presence or absence of tetracycline have a regulatory function not present in the parent. This screen is able to identify populations of vectors with new phenotypes, i.e., Cam$^R$, Tet$^R$, and GFP expression when different combinations of tetracycline and IPTG are used.

The described properties of these vectors may be enhanced further by additional rounds of insertion, rounds of deletion, or by shuffling, using the same screen described supra (and, e.g., assaying for increased levels of GFP expression) or other screens.

EXAMPLE II

Production of a β-Lactamase Containing an In Vivo Biotinylation Peptide

This example demonstrates the generation of a high-activity beta-lactamase polypeptide that contains an in vivo biotinylation sequence. The beta-lactamase gene is capable of conferring ampicillin resistance when expressed in a bacterium; the biotinylation sequence may be used to detect or purify a polynucleotide comprising the high-activity beta-lactamase polypeptide. This example is illustrative of the creation of a novel multifunctional polypeptide using the techniques of the invention.

A) The bla gene (encoding beta-lactamase) is PCR amplified from pUC19 using the primers Bla.For and Bla.Rev and subsequently cloned into the SfiI restriction site of pAK200 (Krebber et al., 1997, *J. Immunol. Meth.* 201:35–55). The resulting vector, pAK200SAMP is randomly linearized (but not phosphorylated) as described in Example I, supra.

A double-stranded 90-bp polydeoxyribonucleotide is generated by annealing of 90-mers Bio.Rev and Bio. For (encoding a polypeptide having an in vivo biotinylation site sequence (Schatz, 1993, *Bio/Technology* 11:1138–1143), added in excess, and ligated to the randomly linearized pAK200SAMP vector at random positions. The in vivo biotinylation site becomes biotinylated when the protein is expressed in *E. coli* strains which express the endogenous biotin holoenzyme synthetase encoded by birA (Barker et al., 1981, *J. Mol. Biol.* 146:451–467).

The pAK200SAMP vector is cleaved with SfiI. The fragment containing the bla gene and a 90 bp insertion is identified by size and gel purified by standard methods. The fragment including the biotinylation sequence is approximately 896 bp (compared to approximately 806 bp without the insert). The purified fragments are cloned into the SfiI site of phage display vector pAK200 (Krebber et al., 1997, supra). After transformation of the phagemid library, the bacteria are spread on 2YT-agar plates containing 30 µg/ml chloramphenicol and a concentration of ampicillin that reduces the recovery from the transformation to 50% of the measured complexity (measured complexity is assessed by plating on 2YT-agar containing 30 µg/ml chloramphenicol; hereinafter "2YT-Cam30" plates).

After growth overnight at 30° C., the plates are scraped and resuspended in 2YT. An aliquot is added to 100 ml 2YT-Cam30 containing the above calculated concentration of ampicillin. After coinfection with VCSM13 (Stratagene) according to Krebber et al., 1997, supra, and growth, the phages are precipitated and panned in PBS/dialyzed 2% skim milk for two to four rounds against streptavidin (Hawkins et al., 1992, *J. Mol. Biol.* 226:889–896) immobilized on magnetic beads (Dynal). The binding of single clones to streptavidin is verified by phage ELISA (Lindner et al., 1997, *Biotechniques* 22:140–49). These clones (which are heterogeneous) are referred to as "pAK200-bla-bio." The combination of the selection on ampicillin plates and the panning procedure identifies polynucleotides encoding an active beta-lactamase gene containing a biotinylation sequence.

B) The expression and beta-lactamase activity of the pAK200-bla-bio produced in Section A, supra, is optimized by PCR shuffling (Stemmer, 1994, *Nature* 370:389–391). To do this, five to ten pAK200-bla-bio species (clones) are selected based on comparatively high beta-lactamase activity (as assessed by conferring on host bacteria resistance to high ampicillin concentrations). The bla-bio insertion is amplified by PCR using Bla.For and BlaRev primers. According to a standard PCR shuffling protocol (Stemmer, 1994, *Nature*, supra), the PCR products are fragmented randomly by DNAse I, reassembled and cloned into the SfiI sites of pAK200SAMP. The library is grown overnight at 30° C. on 2YT-Agar containing 30 µg/ml chloramphenicol and a concentration of ampicillin (the "limiting" concentration) which reduces the recovery from the transformation to 25% of the measured complexity when grown on plates lacking ampicillin. As described supra, the library is scraped from the plates, grown in the presence of the limiting concentration of ampicillin, and coinfected with helper phage (supra) to produce phage particles presenting bla-bio fusion insertions. Those phage particles are again panned against streptavidin beads (supra). Additional shuffling rounds are carried out using selection conditions in which the ampicillin concentration is increased, and temperatures for growth, selection and panning are increased to 37° C. This allows the further optimization of the bla-bio insertion fusions with respect to activity, biotinylation level, folding and stability. The fusion(s) with optimal activity can be used for quantitation of streptavidin, e.g., by measuring beta-lactamase activity in a sandwich ELISA.

TABLE I

| Primers, Oligonucleotides, Polynucleotides | |
| --- | --- |
| GFP.For AAGGAGATATACATATGGCTAGCAAAGGAGAAG | (SEQ ID NO: 1) |
| GFP.Rev TTCACAGGTCAAGCTTCATTATTTGTAGAGCTCATC | (SEQ ID NO: 2) |
| Tet.For TTAAGACCCACTTTCACATTTAAG | (SEQ ID NO: 3) |
| Tet.Rev CTAAGCACTTGTCTCCTGTTTAC | (SEQ ID NO: 4) |
| Opl.For CACTCTATCATTGATAGAGT | (SEQ ID NO: 5) |
| | (SEQ ID NO: 6) |

TABLE I-continued

Primers, Oligonucleotides, Polynucleotides

Op1.Rev  ACTCTATCAATGATAGAGTG

Op2.For  TCCCTATCAGTGATAGAGAA  (SEQ ID NO: 7)

Op1.Rev  TTCTCTATCACTGATAGGGA  (SEQ ID NO: 8)

Bla.For  TATTACTCGCGGCCCAGCCGGCCTTTGCTCACCCAGAAAC  (SEQ ID NO: 9)

Bla.Rev  TAGAATTCGGCCCCCGAGGCCAATGCTTAATCAGTGA  (SEQ ID NO: 10)

Bio.For  GGTTCTGAAGGTGGTGGTTCTGCTCAGCGTCTGTTCCACATCCTGG  (SEQ ID NO: 11)
ACGCTCAGAAAATCGAATGGCACGGTCCGAAAGGTGGTTCTGGT

Bio.Rev  ACCAGAACCACCTTTCGGACCGTGCCATTCGATTTTCTGAGCGTCC  (SEQ ID NO: 12)
AGGATGTGGAACAGACGCTGAGCAGAACCACCACCTTCAGAACC

Many modifications and variations of this invention can be made without departing from its spirit and scope, as will be apparent to those skilled in the art. The specific embodiments described herein are offered by way of example only, and the invention is to be limited only by the terms of the appended claims, along with the fill scope of equivalents to which such claims are entitled.

All references cited herein are incorporated herein by reference in their entirety and for all purposes to the same extent as if each individual publication or patent application was specifically and individually indicated to be incorporated by reference in its entirety for all purposes.

What is claimed is:

1. A method of producing a recombinant polynucleotide having a desired functional property, said method comprising:
   a) mutating a first substrate population of polynucleotides encoding a polypeptide by making deletions from a first nuclease susceptible end using an exonuclease, whereby a first population of deleted polynucleotide segments is produced;
   b) mutating a second substrate population of polynucleotides encoding a polypeptide by making deletions from a second nuclease susceptible end using an exonuclease, whereby a second population of deleted polynucleotide segments is produced;
   c) ligating deleted polynucleotide segments produced in (a) to deleted polynucleotide segments produced in (b) to produce a mixture of recombinant polynucleotides; and,
   d) screening the mixture of recombinant polynucleotides to identify at least one recombinant polynucleotide with a desired functional property.

2. The method of claim 1, further comprising the step of subjecting one or more recombinant polynucleotides identified in step (d) to DNA shuffling.

3. The method of claim 1, wherein the screening in step (d) is for polynucleotides that encode a polypeptide having a functional activity selected from the group consisting of:
   a) an enzymatic activity;

b) a binding activity; and, c) stability to denaturation.

4. The method of claim 3, wherein the activity is an enzymatic activity.

5. The method of claim 1, wherein the substrate populations of polynucleotides comprise a plurality of polynucleotides having the same sequence.

6. The method of claim 1, wherein the substrate populations comprise a mixture of polynucleotides having related sequences.

7. The method of claim 6, wherein the related sequences comprise a family of related genes.

8. The method of claim 6, wherein the related sequences comprise homolog genes from different species.

9. The method of claim 1, wherein recombinant polynucleotides of step (d) are subjected to at least one additional cycle of mutagenesis and screening.

10. The method of claim 9, wherein at least one additional cycle of mutagenesis and screening comprises conducting a polynucleotide amplification process on overlapping segments of recombinant polynucleotides of step (d) under conditions whereby one segment serves as a template for extension of another segment, thereby generating a further population of recombinant polynucleotides and screening the further population of recombinant polynucleotides for a desired property.

11. The method of claim 1, further comprising isolation or enrichment for at least one selected recombinant polynucleotide sequence having the desired functional property.

12. The method of claim 2, wherein the shuffling is performed in vitro.

13. The method of claim 3, wherein the activity is a binding activity.

14. The method of claim 3, wherein the activity is stability to denaturation.

15. The method of claim 10, wherein the overlapping segments comprise random fragments.

16. The method of claim 10, wherein the overlapping segments are produced by random fragmentation.

17. The method of claim 16, wherein the the overlapping segments are produced by random fragmentation with a DNase.

18. The method of claim 10, wherein the overlapping segments comprise oligonucleotides.

19. The method of claim 10, wherein the overlapping segments are produced by a polymerase chain reaction (PCR), wherein one or more recombinant polynucleotides of step (d) serves as a template.

20. The method of claim 19, wherein the polymerase chain reaction is an error-prone polymerase chain reaction (PCR).

21. The method of claim 10, wherein the overlapping segments are produced by cleavage of one or more recombinant polynucleotides of step (d).

* * * * *